United States Patent [19]

Nishihira et al.

[11] Patent Number: 4,978,766
[45] Date of Patent: Dec. 18, 1990

[54] PROCESS FOR PRODUCING 2-HYDROXYMETHYLENE-3,3-DIALKOXY-PROPANENITRILE ALKALI METAL SALT AND PROCESS FOR OBTAINING ALCOHOLIC SLURRY OF SAID COMPOUND FROM ITS SYNTHETIC REACTION MIXTURE

[75] Inventors: Keigo Nishihira; Shuzo Fujikawa, both of Ube; Masayoshi Yamashita, Tokyo, all of Japan

[73] Assignee: UBE Industries, Ltd., Ube, Japan

[21] Appl. No.: 302,059

[22] Filed: Jan. 25, 1989

Related U.S. Application Data

[63] Continuation-in-part of Ser. No. 150,016, Jan. 29, 1988, abandoned.

[30] Foreign Application Priority Data

Feb. 17, 1987 [JP] Japan ................... 62-32381
Feb. 17, 1987 [JP] Japan ................... 62-32382

[51] Int. Cl.$^5$ ................. C07C 253/30; C07C 253/34; C07C 255/07
[52] U.S. Cl. .................... 558/353; 558/448; 558/451
[58] Field of Search .......... 558/353, 451, 448

[56] References Cited

U.S. PATENT DOCUMENTS 3,211,778 10/1965 Kollonitsch ............ 558/353
3,742,017 6/1973 Miyashiro et al. ......... 558/353
4,228,047 10/1980 El-Chahawi et al. ......... 558/451 X
4,525,310 6/1985 Thets et al. ............ 558/353

FOREIGN PATENT DOCUMENTS 12381 3/1959 Japan .
54-84526 7/1979 Japan .
55-167233 12/1980 Japan .
56-88801 7/1981 Japan .
56-125212 10/1981 Japan .
32315 5/1982 Japan .
58-128356 7/1983 Japan .
61-21623 5/1986 Japan .

Primary Examiner—Joseph Paul Brust
Attorney, Agent, or Firm—Frishauf, Holtz, Goodman & Woodward

[57] ABSTRACT

There are disclosed a process for producing a 2-hydroxy-methylene-3,3dialkoxypropanenitrile alkali metal salt (ALVM$_2$) represented by the formula (I):

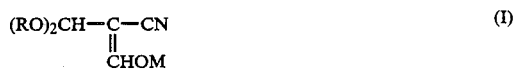

wherein R represents a lower alkyl group having 1 to 4 carbon atoms and M represents an alkali metal, which comprises allowing a 3,3-dialkoxypropanenitrile represented by the formula (II):

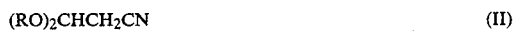

wherein R is the same as defined above, to react with carbon monoxide in a lower alcoholic solution of an alkali metal lower alkoxide; and a process for obtaining ALVM$_2$-alcohlic slurry, which comprises adding a lower alcohol having 1 to 4 carbon atoms to a synthetic reaction mixture containing ALVM$_2$ represented by the above formula (I) and methyl formate and heating the mixture to 30° to 70° C., thereby taking methyl formate out of the system.

9 Claims, 1 Drawing Sheet

FIG. I
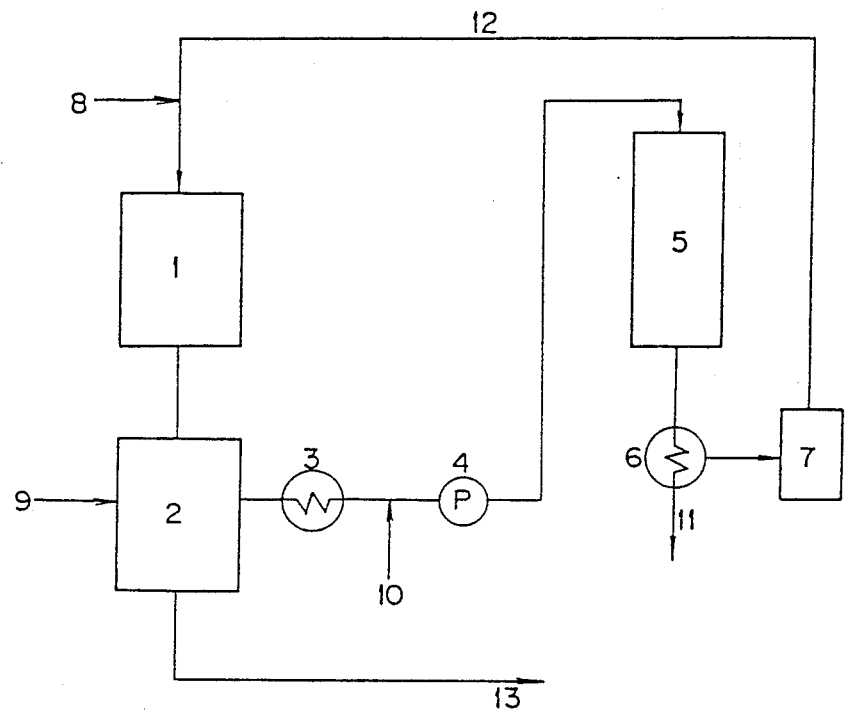

PROCESS FOR PRODUCING 2-HYDROXYMETHYLENE-3,3-DIALKOXY-PROPANENITRILE ALKALI METAL SALT AND PROCESS FOR OBTAINING ALCOHOLIC SLURRY OF SAID COMPOUND FROM ITS SYNTHETIC REACTION MIXTURE

This application is a continuation-in-part of application Ser. No. 7,150,016, filed Jan. 29, 1988, now abandoned.

BACKGROUND OF THE INVENTION

This invention relates to a process for producing 2-hydroxymethylene-3,3-dialkoxypropanenitrile alkali metal salt and a process for obtaining alcoholic slurry of said compound from its synthetic reaction mixture.

2-hydroxymethylene-3,3-dialkoxypropanenitrile alkali metal salt (hereinafter called "ALVM$_2$") is useful as the synthetic intermediate for vitamin B$_1$, and has been produced from 3,3-dialkoxypropanenitrile (hereinafter called "DAPN") according to the normal pressure methyl formate process (Japanese Provisional Patent Publication No. 9755/1985) or the high pressure carbon monoxide process (Japanese Provisional Patent Publication No. 84526/1979 and Japanese Patent Publication No. 21623/1986), of which the latter is said to be more advantageous.

The normal pressure process is a process, in which the reaction between DAPN and methyl formate is carried out in the presence of an alkali metal alcoholate, and the reaction is permitted to proceed by expelling the methanol formed by the reaction out of the system. The high pressure carbon monoxide process is a process in which DAPN, carbon monoxide and methanol are allowed to react in the presence of an alkali metal alcoholate. In either process, a large amount of methyl formate coexists in the reaction mixture after completion of the reaction.

In spreading the methyl formate from the ALVM$_2$ obtained by the reaction, it is important to obtain a slurry with good flowability without deterioration of ALVM$_2$ and methyl formate. Further, if methyl formate can be taken out of the system, the reaction can be made more economical by reutilization thereof.

Methyl formate can be expelled out of the system by filtration or drying.

However, according to the method by drying filtration, because methyl formate has a boiling point of 31.5° C. and an ignition point of −19° C., which are both low, and also exhibits excessive toxicity to human body, special care is required for separation, recovery operation of methyl formate attached on the crystals, typically filtration operation, such as making the system a closed system, etc. On the other hand, since the filtrate obtained contains dissolved ALVM$_2$ and sodium methylate, etc. remained therein, it cannot be utilized as such, and it is not necessary to perform separation operation such as distillation, etc. Besides, during the separation operation of methyl formate, deterioration (decomposition) of the remaining ALVM$_2$ or decomposition of methyl formate by the catalytic action of sodium methylate are caused to occur, whereby recovery of methyl formate will be lowered.

The method by drying is the method, in which the reaction mixture slurry is led as such into a dryer and dried all at once by evaporation of methyl formate, etc., which may be expected to be an industrially advantageous method and experiments were conducted by use of various dryers provided with functions of stirring blade, etc. As the result, troubles of scaling and solidification particularly at the heat transmission surface occurred, and also deterioration (decomposition) of ALVM$_2$ and lowering in recovery of methyl formate occurred similarly as in the case of the method by filtration. Thus, it may be judged to be industrially practiced with difficulty.

On the other hand, the above known high pressure carbon monoxide process comprises allowing DAPN, carbon monoxide and an alkali metal alkoxide to react in a solvent, including ethers such as ethyl ether, dioxane, tetrahydrofuran, etc.; aromatic hydrocarbons such as benzene, toluene, etc.; and so on.

However, the yield of the desired ALVM$_2$ in the above known high pressure carbon monoxide process is at most about 97%, which cannot be said to be sufficiently satisfactory.

SUMMARY OF THE INVENTION

Accordingly, the present inventors have intensively studied in order to make the yield of the high pressure carbon monoxide process sufficiently satisfactory, and consequently found that the desired product can be obtained substantially quantitatively by carrying out the reaction in a lower alcoholic solution of an alkali metal lower alkoxide.

The present invention concerns a process for producing ALVM$_2$ represented by the formula (I):

(I)

wherein R represents a lower alkyl group having 1 to 4 carbon atoms and M represents an alkali metal,
which comprises allowing a DAPN represented by the formula (II):

(II)

wherein R is the same as defined above, to react with carbon monoxide in a lower alcoholic solution of an alkali metal lower alkoxide.

The present invention also concerns a process for obtaining ALVM$_2$, which comprises adding a lower alcohol having 1 to 4 carbon atoms to a synthetic reaction mixture containing ALVM$_2$ represented by the above formula (I) and methyl formate and heating the mixture to 30° to 70° C., thereby taking methyl formate out of the system.

BRIEF DESCRIPTION OF THE DRAWING

FIG. 1 is a diagram showing the steps in Example 2.

DESCRIPTION OF THE PREFERRED EMBODIMENTS

In the above formulae (I) and (II), the lower alkyl group represented by R may be exemplified by a methyl group, an ethyl group, a propyl group, an isopropyl group, a butyl group, an isobutyl group, a sec-butyl group and a tertbutyl group. In the above formula (I), the alkali metal represented by M may be include sodium, potassium, lithium, etc.

The lower alcohol to be used in the present invention is a lower alcohol having 1 to 4 carbon atoms, as exemplified by methyl alcohol, ethyl alcohol, propyl alcohol, isopropyl alcohol, butyl alcohol, isobutyl alcohol, sec-butyl alcohol and tert-butyl alcohol, etc.

The alkali metal lower alkoxide to be used in the present invention corresponds to the above lower alcohol.

In the present invention, the "lower alcoholic solution" is interpreted in substantial meaning, and does not exclude inclusion of other solvents such as ethers, aromatic hydrocarbons to the extent which does not impair the effect of the present invention, namely the improvement of the yield of the desired product.

The amount of the alkali metal lower alkoxide employed may be generally 1.0 to 1.3 moles, preferably 1.03 to 1.15 moles, per one mole of DAPN. If the amount of the alkali metal lower alkoxide to DAPN is less than 1 mole, coloration of the product in the subsequent reaction process for preparing vitamin $B_1$ occurs and the usage (an amount of acetamidine necessary for producing $ALVM_2$) of acetamidine increases. On the other hand, if it exceeds 1.3 moles, the usage of the alkali metal lower alkoxide increases and, as a result, there is no merit practically. Also, excess lower alcohol is necessarily introduced in the reaction system requiring increased usage of CO to convert the alcohol into formate. The concentration of the alkali metal lower alkoxide in the lower alcoholic solution may be generally 20 to 35% by weight, preferably 24 to 30% by weight. If the concentration of the alkali metal lower alkoxide exceeds 35% by weight, precipitation of crystal, etc. of the alkali metal lower alkoxide will occur at 0° C., whereby handling of the material becomes practically difficult. Also, the concentration of the alkali metal lower alkoxide becomes higher than the above range, decomposition of the alkoxide by reaction with ($RONa + H_2O \rightarrow ROH + NaOH$) occurs easily so that quality control of the resulting product becomes difficult. On the other hand, if it is less than 20% by weight, the amount of alcohol introduced increases so that the amount of carbon monoxide supplied or required is also increased to ensure a high yield for the reaction. The result is an increase in costs. Therefore, operation outside the disclosed parameters is not practical. The pressure of the carbon monoxide gas delivered into the system may be generally 20 to 100 kg/cm² (gauge pressure), preferably 30 to 60 kg/cm² (gauge pressure). The reaction temperature may be generally 20° to 100° C., preferably 40° to 60° C. The reaction time depends on the reaction temperature and an amount of the lower alcohol remaining in the reaction system. If the reaction temperature is relatively high, the reaction proceeds rapidly thereby reducing the reaction time to a relatively short period. But if the reaction temperature is too high, the desired product decomposes thereby reducing the yields recovered. In order to obtain a high yield of the product, the amount of the residual alcohol in the reaction system should be decreased as little as possible. Thus, the alcohol in the system becomes 10% by weight or less preferably 5% by weight or less. The reaction time is preferably controlled so as to give a sufficient yield of, for example 90% or higher, preferably 98% or higher of the desired product, and may be generally 0.1 to 10 hours, preferably 0.5 to 5 hours.

In the production process of the present invention, a lower alkyl formate will be by-produced through the reaction between carbon monoxide and the lower alkyl formate.

Accordingly, if the lower alkyl formate or the mixture thereof with the lower alcohol is treated with a pyrolysis catalyst and the carbon monoxide generated is used as the starting material, the present invention can be made further economical.

As the method for taking out the lower alkyl formate from the reaction mixture, there may be employed, for example, the method according to filtration and the method in which a lower alcohol having 1 to 4 carbon atoms is added and the lower alkyl formate is distilled under normal pressure or reduced pressure.

Particularly, when the lower alkyl formate is methyl formate, after the above lower alcohol is added to the reaction mixture, the mixture should preferably be heated to 30° to 70° C. under normal pressure. If the treatment temperature is lower than 30° C., methyl formate cannot be taken out of the system, while if it is over 70° C., $ALVM_2$ which is the product will be decomposed. Said treatment temperature should be particularly preferably 40° to 60° C. The treatment time depends on the treatment temperature since when the temperature is too high, the obtained $ALVM_2$ decomposes, while when it is too low, the treatment time becomes too long. Thus, the treatment should be carried out so as to depress decomposition of $ALVM_2$ within the range of 5% or less. The treatment time is relative short, for example, 1 to 7 hours at 50° C.

The amount of the lower alcohol added should be preferably 50 to 250% by weight based on the $ALVM_2$ amount in the reaction mixture (calculated as the reaction is effected quantitatively), more preferably 80 to 200% by weight.

The synthetic reaction mixture of $ALVM_2$ to be used in the present invention may be any one, provided that it contains $ALVM_2$ and methyl formate, irrespectively whether it is obtained by the normal pressure methyl formate process or the high pressure methyl formate process, and also includes reaction mixture according to other synthetic processes.

In the present invention, for taking out methyl formate out of the system, distillation is conducted generally under normal pressure, but distillation under reduced pressure may be also feasible.

As the method for decomposing a lower alkyl formate into carbon monoxide and the lower alcohol, there may be employed the methods as disclosed in Japanese provisional Patent Publications Nos. 167233/1980, 32315/1981 (Japanese Patent Publication No. 21482/1982), No. 88801/1981, No. 125212/1981 and No 123811/1982 (Japanese patent publication No. 11525/1984).

The pyrolysis catalyst is not particularly limited, but activated charcoal, zeolite itself or a catalyst containing an alkaline earth metal compound or an alkali metal compound as the active component is particularly preferred. The reaction temperature may be generally 200° to 500° C., preferably 250° to 450° C. The liquid space velocity per one hour (hereinafter called "L.H.S.V.") may be generally 0.1 to 100, preferably 0.5 to 20.

EXAMPLES

The present invention is described in more detail by referring to Examples and Comparative examples, but these are not limitative of the present invention at all.

EXAMPLE 1

Into an autoclave made of stainless steel of 800 ml inner volume were charged 92.3 g (0.803 mole) of 3,3-dimethoxypropanenitrile and 160.7 g (sodium methoxide: 0.833 mole) of a methanolic solution of sodium methoxide and, after the system was internally replaced with nitrogen gas, carbon monoxide gas was injected into the autoclave to a pressure of 40 kg/cm² (gauge pressure), and the mixture was heated to 50° C. under stirring to initiate the reaction. The reduction in pressure accompanied with the progress of the reaction was supplemented with carbon monoxide gas to maintain the pressure at about 40 kg/cm² (gauge pressure). After the reaction for 2 hours, the autoclave was cooled with ice-cold water and the contents were taken out. The crystals obtained were filtered and then vacuum dried to give 132.0 g (Yield: 99.6%) of 2-hydroxymethylene-3,3-dimethoxypropanenitrile sodium salt.

COMPARATIVE EXAMPLE 1

Into an autoclave made of stainless steel of 300 ml inner volume were charged 23.0 g (0.200 mole) of 3,3-dimethoxypropanenitrile and 13.0 g (0.240 mole) of powdery sodium methoxide, 12.8 g (0.400 mole) of methanol and 65 ml of toluene and, after the system was internally replaced with nitrogen gas, carbon monoxide gas was heated to under stirring to initiate the reaction. The reduction in pressure accompanied with the progress of the reaction was supplemented with carbon monoxide gas to maintain the pressure at about 40 kg/cm² (gauge pressure). After the reaction for 3 hours, the autoclave was cooled with ice-cold water and the contents were taken out. The crystals obtained were filtered and then vacuum dried to give 32.0 g (Yield: 96.9%) of 2-hydroxymethylene-3,3-dimethoxypropanenitrile sodium salt.

EXAMPLE 2

Following the steps shown in FIG. 1, 2-hydroxymethylene-3,3-dimethoxypropanenitrile sodium salt was produced.

Into an autoclave (1) made of stainless steel of 20-liter inner volume were charged 2,019 g (17.55 mole) of 3,3-dimethoxypropanenitrile and 3,750 g (sodium methoxide: 18.51 mole) of a methanolic solution of sodium methoxide and carbon monoxide was injected from the supplementing line (8) to a pressure of 40 kg/cm² (gauge), followed by heating of the mixture to 50° C. under stirring to initiate the reaction. The reduction in pressure accompanied with the progress of the reaction was supplemented with carbon monoxide gas to maintain the pressure at about 40 kg/cm² (gauge pressure). At this time, methyl formate may be fed to the methyl formate supplementing line (10) and carbon monoxide gas may be introduced through the carbon monoxide feeding line (12) via the carbon monoxide generating device (5) by decomposition.

The reaction was completed in 4 hours, and 2.58 Nm³ of carbon monoxide was necessary. Most of methanol was found to be converted to methyl formate.

After the pressure in the autoclave (1) was released by cooling, the reaction mixture was transferred into the methyl formate stripper (2), and 5,270 g of methanol was added through the methanol feeding line (9). The methyl formate stripper (2) was heated to 65° C. to distill the methanolic solution of methyl formate, and 7,130 g of a methanolic solution of methyl formate (methyl formate 84.6% by weight) was obtained via the methyl formate condenser (3).

On the other hand, 6,647 g of a methanolic solution containing 2,837 g (17.19 mole) of 2-hydroxymethylene-3,3-dimethoxypropanenitrile sodium salt containing no methyl formate was obtained through the ALVM₂ slurry withdrawing line (13).

The methanolic solution of methyl formate recovered was passed into the carbon monoxide generating device (5) (reaction tube made of stainless steel of 50 mm in diameter × 3,500 mm in length filled with one liter of a catalyst of activated charcoal carried on KCl). The reaction was carried out under the conditions of L.H.S.V. of 2.0 hr⁻¹, pressure of 50 kg/cm² (gauge pressure) and 290° C. The carbon monoxide gas containing methanol exiting from the carbon monoxide generating device (5) was transferred into the condenser (6) to condense methanol, and the gas was delivered to the gas holder (7). Conversion to methyl formate was found to be 99.4% and the gas in the gas holder (7) was carbon monoxide with a purity of 98.0%. Thus, in the carbon monoxide feeding line (12), 0.62 Nm³/hr of carbon monoxide was generated. Further, 1,160 g/h of methanol was recovered from the recovered methanol withdrawing line (11). Conversion was 97.8% based on methyl formate.

On the other hand, in the autoclave (1), charging of the starting materials for production of 2-hydroxymethylene-3,3-dimethoxypropanenitrile sodium salt for the next time had been completed, and the reaction could be carried out by controlling the pressure in the autoclave (1) with the gas from the carbon monoxide feeding line (12). Carbon monoxide corresponding to shortage was fed from the bomb through the carbon monoxide supplementing line (8). At this time, methyl formate may be fed to the methyl formate supplementing line (10) and carbon monoxide gas may be introduced through the carbon monoxide feeding line (12) via the carbon monoxide generating device (5) by decomposition.

Also, the methanol recovered from the recovered methanol withdrawing line (11) was found to have a quality sufficiently satisfactory for preparation of the methanolic solution in the ALVM₂ slurry withdrawing line (13), and this can be also used in the methanol feeding line (9).

EXAMPLE 3

The reaction mixture slurry obtained in the same amounts of the starting materials and the same manner as in Example 1 was transferred into a round bottom flask of one liter volume equipped with a Claisen type distillation device, a condenser and a stirrer, and 253 g of methanol was added thereto. The flask was heated under stirring to evaporate methyl formate. The end point of this separation procedure was when the inner temperature in the flask reached 65° C. In 339.7 g of the distillate, 68.3% by weight of methyl formate was found to be contained, and the recovery as calculated from the methyl formate amount measured by gas chromatogram immediately after the above reaction was 98.1%. Also, the weight of the flask residual solution was 310.5 g and according to the result of analysis by liquid chromatogram, it was found to contain 42.1% by weight of 2-hydroxymethylene-3,3-dimethoxypropanenitrile as calculated on sodium salt, which corresponded to a yield of 98.7% based on 3,3-dimethoxypropanenitrile provided for the reaction in Example 1.

COMPARATIVE EXAMPLE 2

The reaction mixture slurry obtained by use of the same device and method as in Example 1 except for using 90.1 g (0.784 mole) of 3,3-dimethoxypropanenitrile was passed through a pressure filter device mounted with a filter cloth made of polypropylene with a gas permeation amount of 0.8 ml/cm² sec without applying any cooling means, and under pressurization with nitrogen gas to 2.5 kg/cm² (gauge pressure), sodium salt of 2-hydroxymethylene-3,3-dimethoxypropanenitrile was separated.

The crystals were dried in a vacuum dryer equipped with a condenser by dry ice-acetone bath cooling of a vacuum degree of 60 Torr and a temperature of 50° C. to obtain 21.7 g of 2-hydroxymethylene-3,3-dimethoxypropanenitrile sodium salt and 31.7 g of the condensate (methyl formate 87.4%). The sodium salt was obtained in a yield of 92.7% based on 3,3-dimethoxypropanenitrile. On the other hand, the filtrate containing 80.2% by weight of methyl formate was evaporated by a Claisen distillation device at the final temperature of 65° C. to remove methyl formate. During the distillation operation, generation of gas which was considered to be formed by decomposition of methyl formate was observed, and formation of carbon monoxide was recognized. The methyl formate was distilled in an amount of 148.4 g, and the recovery combined with the methyl formate recovered during drying amounted to 88.1%.

The residual solution in the flask was dark brown viscous material, and 1.4 g of 2-hydroxymethylene-3,3-dimethoxypropanenitrile was found to be contained therein, but it was unrecoverable because of the co-present impurities.

COMPARATIVE EXAMPLE 3

The reaction mixture slurry obtained by use of the same device and method as in Example 1 except for using 91.2 g (0.793 mole) of 3,3-dimethoxypropanenitrile was charged into a jacketed stirring tank of one liter inner volume equipped with a Claisen type distillation device, a condenser and provided with a stirring blade made of a resin which contacts gently the inner wall, and methyl formate was evaporate by heating by passing hot water of 70° C. through the jacket side. About 10 minutes after initiation of distilling out, formation of scale was observed on the inner wall of the tank, whereby heat transmission state, stirring state became bad to enable no stable drying, and drying was discontinued after one hour. Also, on the stirring shaft, crystals were attached in a mass, and they could be taken out in the crystal state out of the system with difficulty. Also, the brown matter hardly attached on the vessel wall contained a portion even difficultly soluble in methanol, which was apparently found to be deteriorated. According to the result of analysis by liquid chromatogram obtained by dissolving the whole amount in water, the 2-hydroxymethylene-3,3-dimethoxypropanenitrile sodium salt was obtained in an amount of 122.6 g, which corresponded to a yield of 93.7% based on 3,3-dimethoxypropanenitrile used for the reaction.

According to the present invention, ALVM₂ can be produced substantially quantitatively with a yield of 98% or more.

Also, according to the present invention, a reaction mixture slurry of ALVM₂ containing a large amount of methyl formate and unstable to heat can be obtained without contact with the outer air, and without deterioration of ALVM₂ and methyl formate with good slurry state, and at high yield.

We claim:

1. A process for producing a 2-hydroxymethylene-3,3-dialkoxypropanenitrile alkali metal salt represented by the formula:

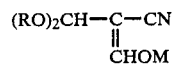

wherein R represents a lower alkyl group having 1 to 4 carbon atoms and M represents an alkali metal, which process consists of reacting at a temperature of 20° C. to 100° C., a 3,3-dialkoxypropanenitrile represented by the formula:

wherein R is the same as defined above, with carbon monoxide at a pressure of 20 to 100 kg/cm² (gauge), in a lower alcoholic solution of an alkali metal lower alkoxide, wherein the amount of the alkali metal lower alkoxide is 1.0 to 1.3 moles per one mole of 3,3-dialkoxypropanenitrile and the concentration of the alkali metal lower alkoxide in the lower alcoholic solution is 20 to 35% by weight; until the concentration of lower alcohol in the reaction mixture is 10% or less by weight.

2. The process according to claim 1, wherein a lower alkyl formate by-produced or the mixture of said lower alkyl formate with the lower alcohol is treated with a pyrolysis catalyst and the carbon monoxide generated is used as the starting material.

3. The process according to claim 2, wherein said lower alkyl formate is methyl formate.

4. A process for obtaining a 2-hydroxymethylene-3,3-di-alkoxypropanenitrile alkali metal salt-alcohol slurry, which comprises adding a lower alcohol having 1 to 4 carbon atoms to a synthetic reaction mixture containing 2-hydroxymethylene-3,3-dialkoxypropanenitrile alkali metal salt represented by the formula:

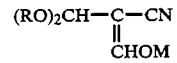

wherein R represents a lower alkyl group having 1 to 4 carbon atoms and M represents an alkali metal; and
  methyl formate; and
  heating the mixture to 30° to 70° C., thereby taking methyl formate out of the system and wherein said heating is carried out so that the decomposition of 2-hydroxymethylene-3,3-dialkoxypropanenitrile alkali metal salt is depressed to within 5% by weight or less.

5. The process according to claim 1 wherein the lower alkoxide is a C₁–C₄ alkoxide.

6. The process according to claim 5, wherein the reaction is carried out until the concentration of the lower alcohol is 5% by weight or less.

7. The process according to claim 4, wherein an amount of the lower alcohol added is 50 to 250% by weight based on the amount of 2-hydroxymethylene-3,3-dialkoxypropanenitrile alkali metal salt.

8. The process according to claim 4, wherein the heating is carried out until the concentration of the lower alcohol in the reaction system is 10% by weight or less.

9. The process according to claim 8, wherein the reaction is carried out until the concentration of an alcohol in the reaction system is 5% by weight or less.

* * * * *